(12) United States Patent
Fateh et al.

(10) Patent No.: US 6,244,711 B1
(45) Date of Patent: Jun. 12, 2001

(54) ERGONOMIC SYSTEMS AND METHODS FOR OPERATING COMPUTERS

(75) Inventors: Sina Fateh, Sunnyvale; James F. Flack, Los Altos Hills, both of CA (US)

(73) Assignee: Vega Vista, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/476,921

(22) Filed: Jan. 4, 2000

Related U.S. Application Data (63) Continuation of application No. 09/097,876, filed on Jun. 15, 1998, now Pat. No. 6,076,928.

(51) Int. Cl.⁷ ..................................................... A61B 3/14
(52) U.S. Cl. ............................................................ 351/208
(58) Field of Search .................................... 351/203, 208; 434/43; 396/2, 429; 348/552

(56) References Cited

U.S. PATENT DOCUMENTS

| | | |
|---|---|---|
| D. 376,648 | 12/1996 | Fateh . |
| 2,270,069 | 3/1941 | Martin . |
| 3,388,646 | 2/1966 | Sullivan . |
| 3,468,545 | 8/1966 | Anderson . |
| 3,582,189 | 6/1971 | Moritz . |
| 3,917,278 | 11/1975 | Steinman . |
| 4,067,129 | 1/1978 | Abramson et al. . |
| 4,068,230 | 1/1978 | Schneiter . |
| 4,137,566 | 1/1979 | Haas et al. . |
| 4,294,522 * | 10/1981 | Jacobs ................................... 351/203 |
| 4,365,873 | 12/1982 | Ginsburg . |
| 4,611,893 | 9/1986 | Schrier . |
| 4,714,428 * | 12/1987 | Bunker et al. ......................... 434/43 |

(List continued on next page.)

OTHER PUBLICATIONS

Software Manual for Eye Works 1.0, ICC Group Inc. 1995.
Orthopic Treatment, Chapter 18, pp. 178–201.
Health and Vision "Solving Vision Problems at Computers in the United States," Points de vue N_33, Oct. 1995.
Prio Corporation, "Latest Press Materials" http://www.prio.com, Jun. 13, 1997.
"A Vision Theraphy Software—Eyeworks," http://www.iccgroup.com.Jul. 25, 1996.

*Primary Examiner*—George Manuel
(74) *Attorney, Agent, or Firm*—Hickman, Coleman & Hughes, LLP (57) ABSTRACT

The teachings of the present invention aid a user in attaining an ergonomic position with respect to a remote object such as a display screen (e.g., VDT) or a manufacturing tool. To that end, various mechanisms which feedback to the viewer information related to position and orientation are taught. A first aspect incorporates a feedback mechanism into a display screen. The feedback mechanism could be formed in a variety of manners. In one embodiment, four lights are arranged such that a viewer in the proper orientation will perceive all four lights. However, as the viewer's orientation varies, one or more of the lights is concealed, thereby indicating to the user that the orientation is improper. In another embodiment, the cluster of lights is replaced with a cluster of four distinct pieces of diffraction grating. The diffraction grating could be such that the intensity of the reflected light varies as the viewer's orientation varies. Alternatively, a hologram could arranged such that the image presented to the viewer changes, even presenting informative text to the viewer. Another aspect of the present invention teaches a feedback mechanism that further provides visual feedback regarding position information. In one embodiment, a strip of diffraction grating or other suitable material is applied upon the display screen. The strip is formed such that depending upon the viewers position, the viewer perceives a certain image (e.g., "20 Inches," the color green).

30 Claims, 8 Drawing Sheets

U.S. PATENT DOCUMENTS

| | | |
|---|---|---|
| 4,716,469 | 12/1987 | Kim et al. . |
| 4,831,448 | 5/1989 | Park . |
| 4,944,572 | 7/1990 | Young . |
| 5,051,931 | 9/1991 | Cheu et al. . |
| 5,252,950 | 10/1993 | Saunders et al. . |
| 5,289,200 | 2/1994 | Fidler et al. . |
| 5,311,220 | 5/1994 | Eichenlaub . |
| 5,322,441 | 6/1994 | Lewis et al. . |
| 5,351,963 | 10/1994 | Baek . |
| 5,359,675 | 10/1994 | Siwoff . |
| 5,452,516 | 9/1995 | Schegerin . |
| 5,510,893 | 4/1996 | Suzuki . |
| 5,515,069 | 5/1996 | Dillon, III . |
| 5,570,301 | 10/1996 | Barrus . |
| 5,661,539 | 8/1997 | Sheedy . |
| 5,668,622 | 9/1997 | Charbonnier et al. . |
| 5,686,940 | 11/1997 | Kuga . |
| 5,696,995 * | 12/1997 | Huang et al. .................... 396/2 |
| 5,748,228 | 5/1998 | Kobayashi et al. . |

* cited by examiner

ERGONOMIC SYSTEMS AND METHODS FOR OPERATING COMPUTERS

This is a Continuation of Application Ser. No. 09/097,876 filed on Jun. 15, 1998, now U.S. Pat. No. 6,076,928 the disclosure of which is incorporated herein by reference.

TECHNICAL FIELD

The present invention generally relates to the field of ergonomic work environments. More specifically, the present invention teaches methods and systems for aiding a computer user in finding an ergonomic position within a work environment.

BACKGROUND

Whether working or relaxing, a growing proportion of the world's population spends prolonged periods in fixed, sedentary positions, with their vision and attention focused on a small portion of their environment. For example, office workers are required to work at computer terminals performing tasks such as word processing, data entry, and generating computer graphics. Students are regularly using computers for study and in the classroom. Computers and televisions are commonly viewed for entertainment and information purposes. These types of activities have unintended side effects such as eye fatigue, eye strain, difficulty focusing, headaches, backaches, and general muscular discomfort.

These and other symptoms are often the result of an improper arrangement of the sufferer's environment and his position and orientation within that environment. Often, steps the sufferer may take to alleviate one symptom may in turn cause other, perhaps more subtle, problems. For example, a video display terminal (VDT) user may position himself in a certain manner to avoid back discomfort, yet in so doing end up an improper distance from the VDT, as well as poorly oriented, thereby causing eye fatigue.

James E. Sheedy, in his U.S. Pat. No. 5,661,539, described what he termed a "Visual Tool for Assessing the Ergonomic Position of a Video Display Terminal." Sheedy's Visual Tool consists of a substantially planar measurement tool having a plurality of measurement indicia arranged to indicate the distance above and below a center point of the measurement tool. An alignment indicator, essentially a fabric tape measure, is attached to the center point and can be grasped by a user and extended outward. A VDT user may position the measurement tool over the face of the VDT and then determine a desired vertical orientation and distance from the face of the VDT by use of the Visual Tool. Hence Sheedy's Visual Tool provides the VDT user one manual device for determining his or her position and orientation in front of the VDT. Note, however, that the VDT use cannot simultaneously view the VDT while using Sheedy's Visual Tool.

What are needed are tools for providing a user dynamic visual feedback enabling the use to obtain a proper, ergonomic orientation with the computer work environment.

SUMMARY OF THE INVENTION

The teachings of the present invention aid a user in attaining an ergonomic position with respect to a remote object such as a display screen (e.g., VDT) or a manufacturing tool. To that end, various mechanisms which feedback to the viewer information related to position and orientation are taught. A first aspect incorporates a feedback mechanism into a display screen. The feedback mechanism could be formed in a variety of manners. In one embodiment, four lights are arranged such that a viewer in the proper orientation will perceive all four lights. However, as the viewer's orientation varies, one or more of the lights is concealed, thereby indicating to the user that the orientation is improper. In another embodiment, the cluster of lights is replaced with a cluster of four distinct pieces of diffraction grating. The diffraction grating could be such that the intensity of the reflected light varies as the viewer's orientation varies. Alternatively, a hologram could arranged such that the image presented to the viewer changes, even presenting informative text to the viewer.

Another aspect of the present invention teaches a feedback mechanism that further provides visual feedback regarding position information. In one embodiment, a strip of diffraction grating or other suitable material is applied upon the display screen. The strip is formed such that depending upon the viewers position, the viewer perceives a certain image (e.g., "20 Inches," the color green). In preferred embodiments, the left and right eyes perceive different images such that when the viewer's orientation is improper, the image perceived by one eye is different from the other.

Yet another aspect of the present invention is directed towards ergonomic software capable of executing on a computer system having a sensor capable of measuring the distance between a viewer and a display screen of the computer system. The ergonomic software measures and displays the viewers setback from the display screen, as well as making suggestions regarding preferred font size and viewer position.

BRIEF DESCRIPTION OF THE DRAWINGS

The invention, together with further objectives and advantages thereof, may best be understood by reference to the following description taken in conjunction with the accompanying drawings which are described below.

FIG. 3b illustrates an image of the visual feedback device of FIG. 2 as perceived by a computer user oriented as shown in FIG. 3a.

FIG. 4b illustrates an image of the visual feedback device of FIG. 2 as perceived by a computer user oriented as shown in FIG. 4a.

FIG. 5b illustrates an image of the visual feedback device of FIG. 2 as perceived by a computer user oriented as shown in FIG. 5a.

BEST MODES FOR CARRYING OUT THE INVENTION

The methods and systems of the present invention enable a user to maintain an ergonomic position with respect to a remote object such as a display screen (e.g., VDT) or a manufacturing tool. Failure to achieve a proper position and orientation of a user's viewpoint with respect to a VDT, tool position, calibrated indicator, etc., often causes physical discomfort such as eye fatigue, back strain, etc. The present invention is directed towards simple mechanisms which provide the user meaningful feedback related to both his position and orientation. In the following description of various aspects of the present invention, the VDT example is often used for ease of reference. However, those of skill in the art will recognize that the present invention is not limited by this particular application, but is suitable for other applications such as television displays, tool position indicators, status readouts or any environment wherein a viewer wishes to maintain a particular position.

Figure 1:
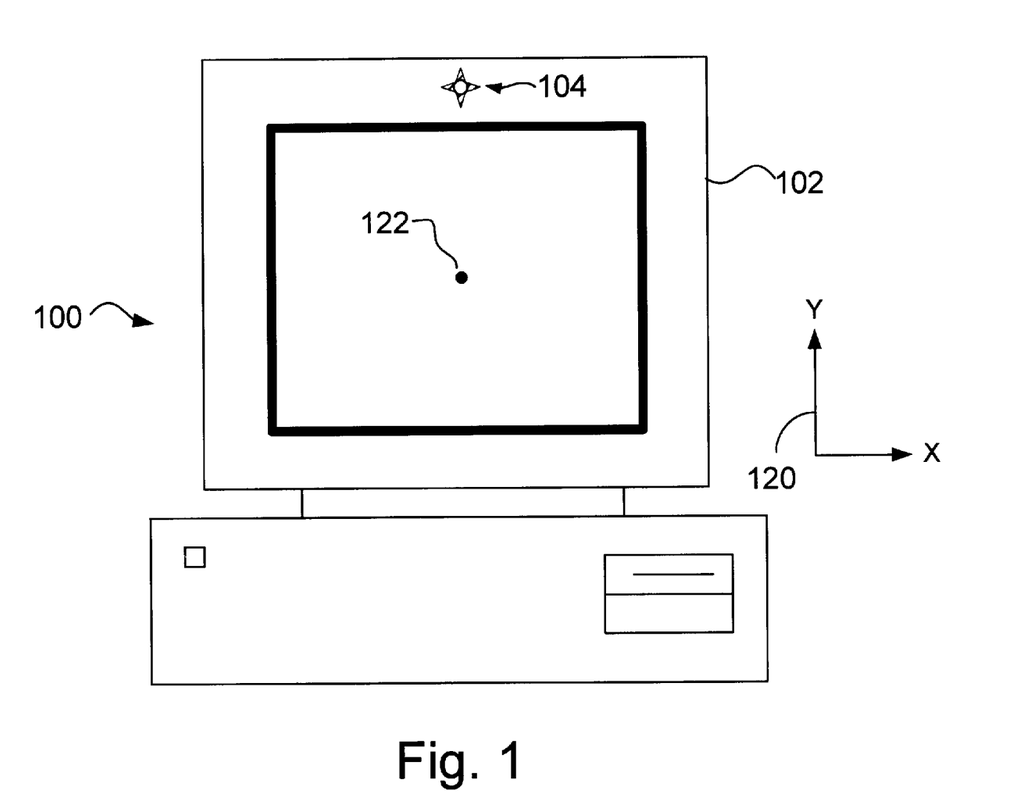
FIG. 1 illustrates a computer system having a visual feedback device in accordance with one embodiment of the present invention.

A first embodiment of the present invention will now be described with reference to FIGS. 1–5. FIG. 1 illustrates a computer system 100 including a display screen 102 and a cluster 104 (exploded in FIG. 2) of four light sources 106–112. The light sources 106–112 are arranged such that a properly oriented viewer will perceive all four light sources as illuminated. As described in more detail below with reference to FIGS. 3a–5b, as the viewer's orientation varies, one or more of the light sources disappears from view, thereby indicating to the viewer that her orientation is improper.

In FIG. 1, orientation refers to a viewers position within an x-y (or horizontal-vertical) axis 120 parallel to the plane of the display panel. It has been found that a suitable orientation for a viewer of a display screen 102 is at about its top, center point. Hence in FIG. 1 the cluster 104 is located at the top, center point of the display screen 102, and is arranged such that all four lights are perceived when the viewer is substantially directly in front of the cluster 104. However, the cluster 104 may be located at a different position (on or off the display screen 102) and/or arranged to appear fully illuminated from different viewer orientations. For example, the cluster 104 may be positioned at the lower left corner of the display screen 102 yet be arranged such that all four lights are perceived when the viewer is substantially oriented at a center point 122 of the display screen.

Figure 2:
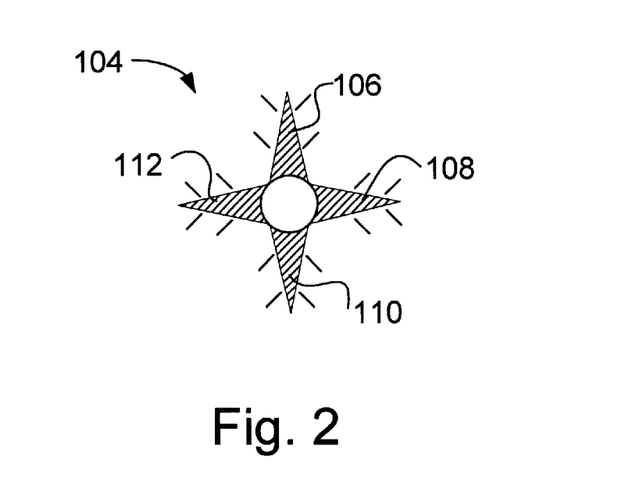
FIG. 2 illustrates a cluster of light sources forming the visual feedback device of FIG. 1.
Figure 3A:
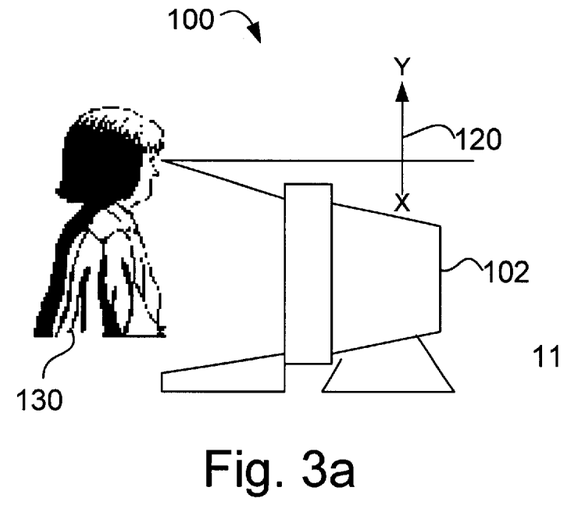
FIG. 3a illustrates a computer user positioned at an orientation above the ideal vertical ergonomic position.
Figure 3B:
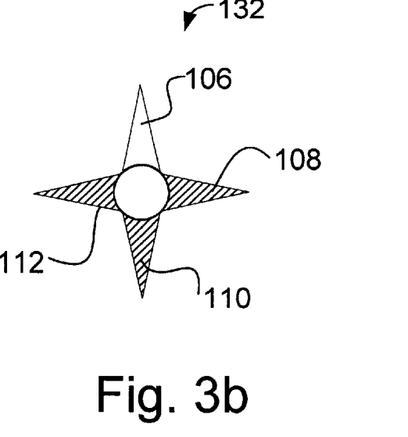
Figure 4A:
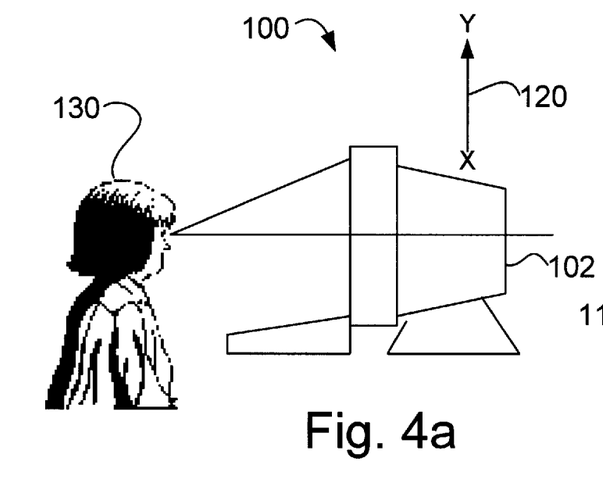
FIG. 4a illustrates a computer user positioned at an orientation below the ideal vertical ergonomic position.
Figure 4B:
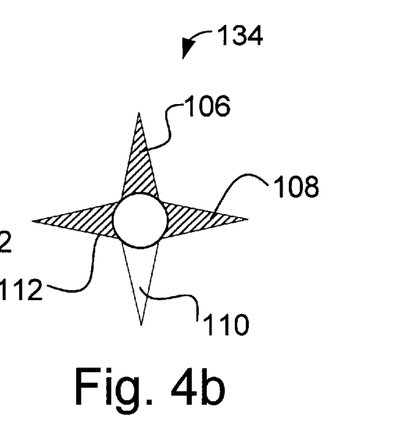
Figure 5A:
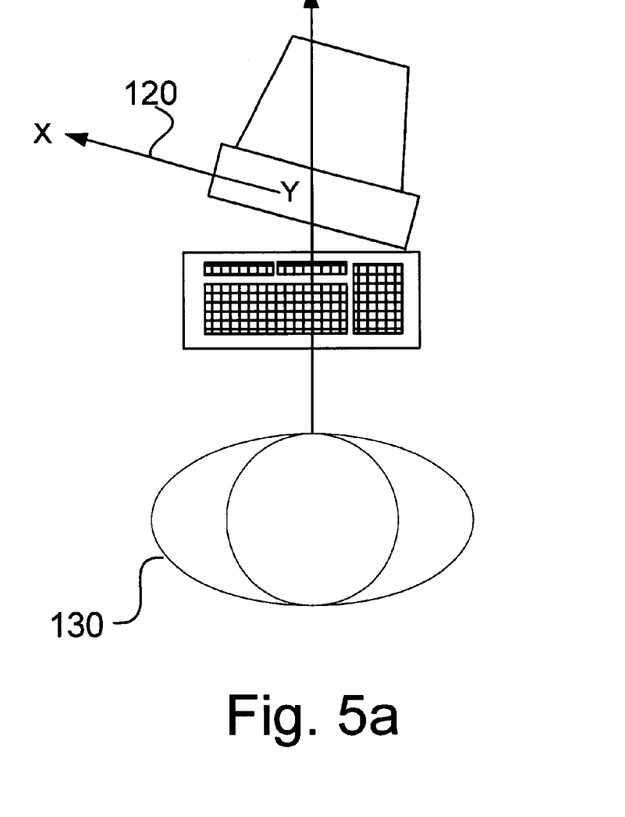
FIG. 5a illustrates a computer user positioned at an orientation off of the ideal horizontal ergonomic position.
Figure 5B:
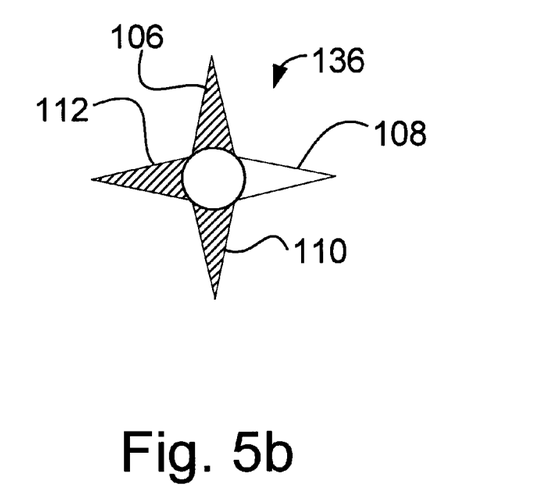

FIG. 2 illustrates the image of the cluster 104 perceived by a viewer that is properly oriented along the x-y axis 120. That is, the properly oriented viewer is capable of perceiving illumination from each of the light sources 106–112. (For the sake of present discussion, the properly oriented viewer is located near or substantially upon the origin of the x-y axis.) FIG. 3a illustrates a viewer 130 whose horizontal orientation is proper but whose vertical orientation is above the origin of the x-y axis 120. FIG. 3b illustrates an image 132 of the cluster 104 that would be perceived by the viewer 130 oriented as in FIG. 3a. Specifically, the viewer 130 perceives the cluster 104 as if the uppermost light source 106 were not illuminated. FIG. 4a illustrates the viewer 130 whose horizontal orientation is proper but whose vertical orientation is below the origin of the x-y axis 120. FIG. 4b illustrates an image 134 of the cluster 104 that would be perceived by the viewer 130 oriented as shown in FIG. 4a. Specifically, the viewer 130 perceives the cluster 104 as if the lowermost light source 110 is not illuminated. FIG. 5a illustrates the viewer 130 whose horizontal orientation is off of the origin of the x-y axis 120. FIG. 5b illustrates an image 136 of the cluster 104 that would be perceived by the viewer 130 oriented as shown in FIG. 5a. Specifically, the viewer 130 perceives the cluster 104 as if the rightmost light source 108 is not illuminated.

As will be appreciated by those skilled in the art, light sources 106–112 may take on any suitable form providing an image that varies with respect to the viewer's orientation. For example, light sources 106–112 may be light emitting sources such as LEDs or light bulbs embedded within the display screen 102, properly recessed within the display screen 102 to achieve the desired result. Alternatively, lenses covering the light emitting sources may focus or polarize the light in order to achieve the desired result. It is also contemplated that light sources 106–112 may be light reflective devices such as a hologram, a lenticular parallax panoramagram variable aspect display, other lenticular devices, diffraction grating, columnates, etc.

Alternatively, the light sources 106–112 could be four distinct pieces of diffraction grating formed such that the intensity of the reflected light varies as the viewer's orientation varies. Hence, rather than providing discrete, illuminated/non-illuminated feedback to the viewer 130, the cluster 104 could provide continuous feedback with the illumination intensity decreasing as the viewer moves further out of orientation. Alternatively, a hologram could be formed such that the image presented to the viewer changes, even presenting informative text to the viewer. (E.g., "MOVE LEFT!" or "MOVE RIGHT!") Such holograms could be implemented in many ways, whether through diffraction grating or lenticular devices.

Another aspect of the present invention teaches a feedback mechanism that provides a viewer visual feedback regarding his or her distance from the display screen. For example, a strip of diffraction grating or other suitable material applied upon the display screen may be formed such that depending upon the viewers position, the viewer perceives a feedback image (e.g., "20 Inches," a green band, a red band). Three separate embodiments of this aspect will now be described with reference to FIGS. 6–6c, FIGS. 7–8, and FIGS. 8–9, respectively.

Figure 6:
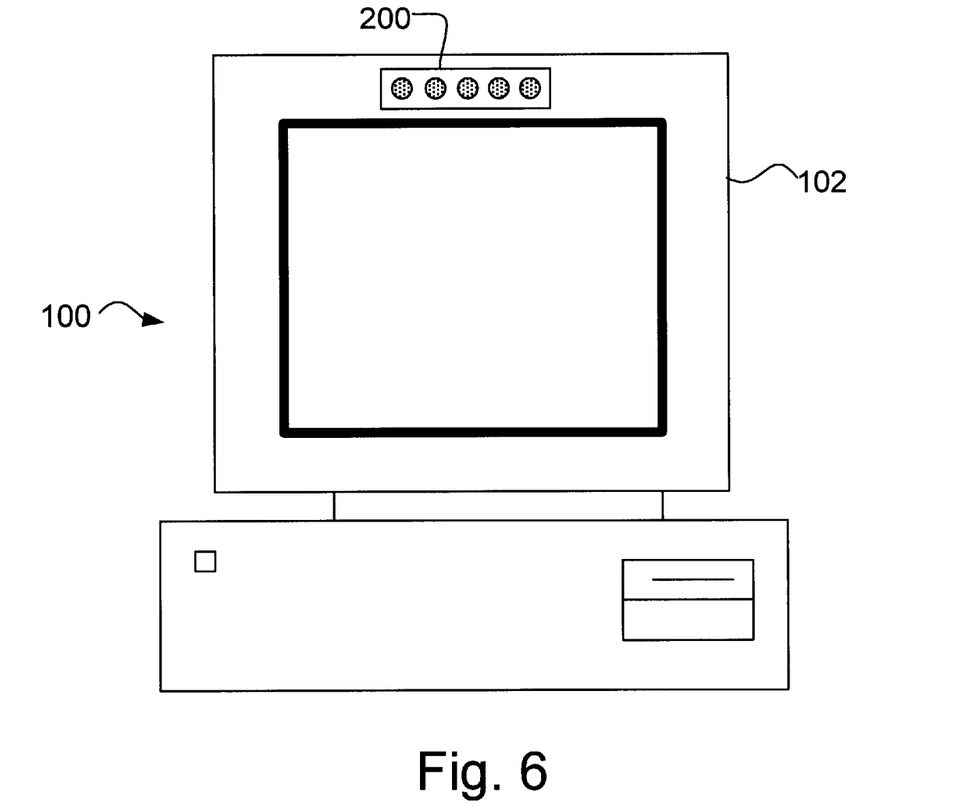
FIG. 6 illustrates a computer system having a visual feedback device in accordance with yet another embodiment of the present invention, the visual feedback device capable of rendering different images dependent upon the distance of the computer user from the computer system.
Figure 6A:
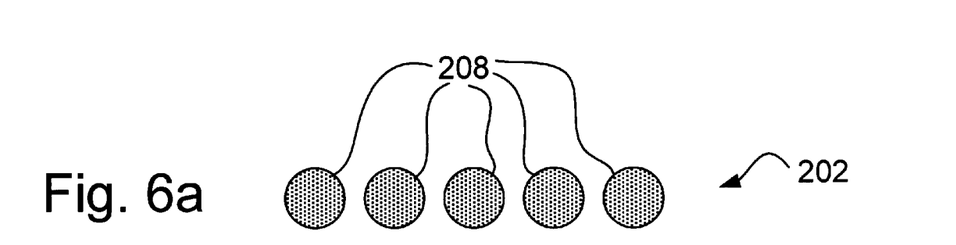
FIGS. 6a–6c illustrate three different images the computer user will perceive at three different distances from the visual feedback device of FIG. 6.
Figure 6B:
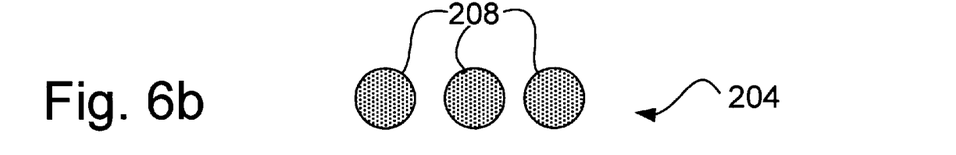
Figure 6C:
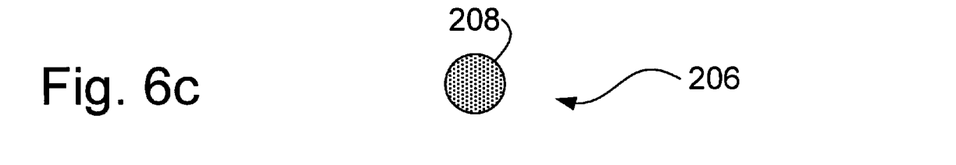

FIG. 6 illustrates a computer system 100 having a display screen 102 with a viewer position feedback device 200 affixed thereto. The viewer position feedback device 200 is capable of presenting three images 202–206 to a viewer situated in front of the display screen 102. An image 202 as in FIG. 6a showing five filled circles 208 will be perceived by the viewer who is positioned about 18 inches (e.g., 18+/−1.0 inches) away from the display screen 102. An image 204 as in FIG. 6b showing three filled circles 208 will be perceived by the viewer who is positioned about 20 inches (e.g., 20+/−1 inches) away from the display screen. An image 206 as in FIG. 6c showing one filled circle 208 will be perceived by the viewer who is positioned about 22 inches (e.g., 22+/−1 inches) away from the display screen.

The filled circles 208 can be presented in different colors to further distinguish the distances. Outside of the optimal viewing range, the image presented by the feedback device 200 could take on any suitable form. For example, the image could be blank, provide textual information ("TOO CLOSE" or "TOO FAR"), or appear as a red strip thus indicating improper viewer positioning.

Figure 7:
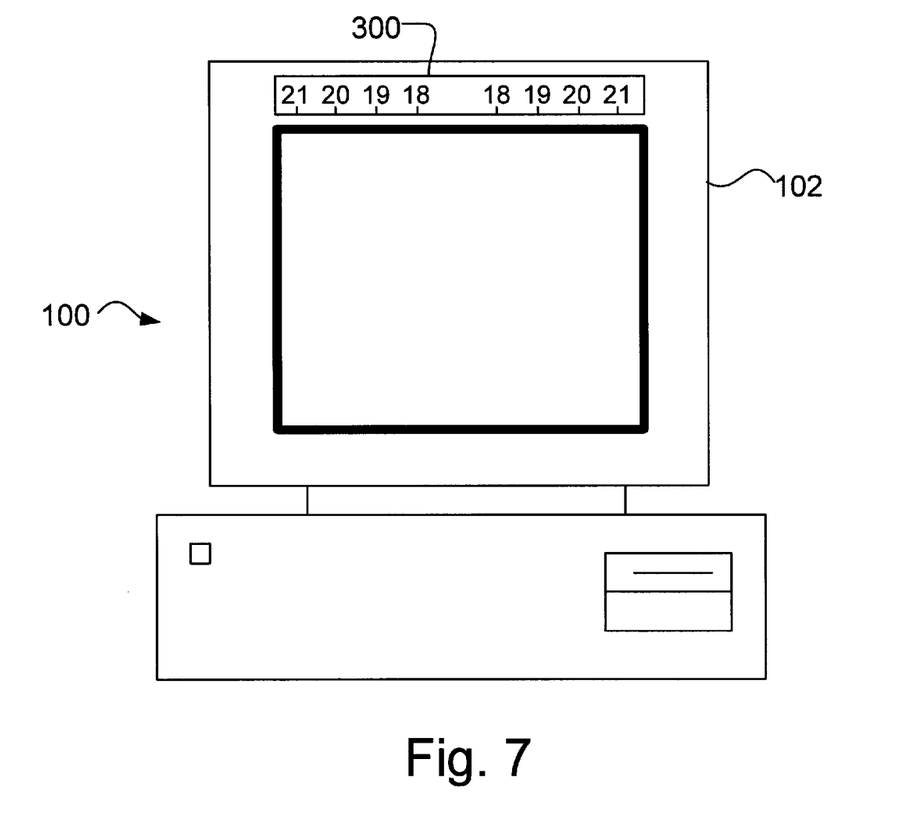
FIG. 7 illustrates a computer system having a visual feedback device in accordance with still another embodiment of the present invention, the visual feedback device capable of rendering different images dependent upon both the computer user orientation and the distance of the computer user from the computer system.
Figure 8:
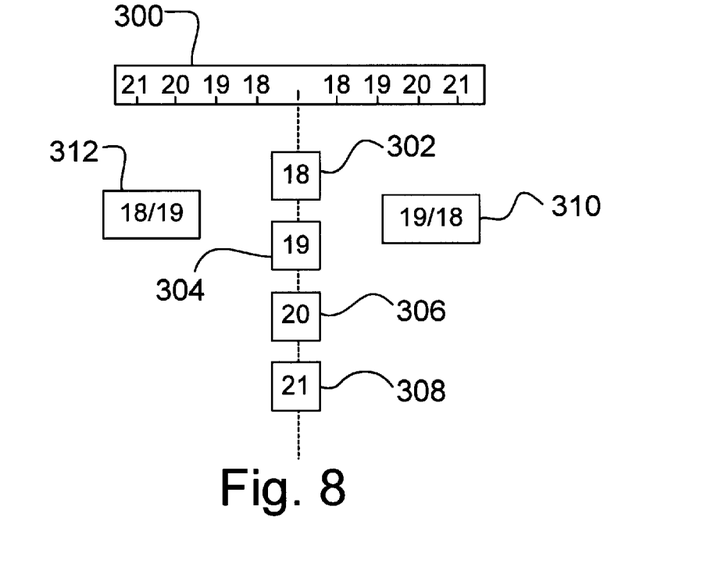
FIG. 8 illustrates several different images the computer user will perceive at different distances from and orientation to the visual feedback device of FIG. 7.

With reference to FIGS. 7–8, yet another embodiment of the present invention will now be described. FIG. 7 illustrates a computer system 100 having a display screen 102 with a viewer position and orientation feedback device 300 affixed thereto. Feedback device 300 as drawn indicates possible images for display, but does not necessarily represent how these images would be formed and arranged on the surface of feedback device 300. Instead, as will be appreciated by those skilled in the art, the arrangement of images on the feedback device will depend upon the technology (e.g., lenticular devices, diffraction grating, etc.) selected for implementation.

As illustrated in FIG. 8, the feedback device 300 is capable of presenting a plurality of images to a viewer situated in front of the display screen 102. Images 302–306 represent images perceived by the viewer when he or she is properly oriented in front of the display screen 102. For example, the image 302 appears as the numeral "18" when the viewer is properly oriented and is positioned about 18 inches from the display screen. Images 310–312 represent images perceived by a viewer improperly oriented in front of the display screen 102. For example, the image 312 appears as a combination or blurring of the numerals "18" and "19," or the image 312 may be implemented to "flicker" back and forth between the numerals depending upon slight variations of the viewer's position. In any event, the perceived image indicates to the viewer a rough estimate of her distance from the display screen 102 but, importantly, also indicates that the viewer is improperly oriented.

Figure 9:
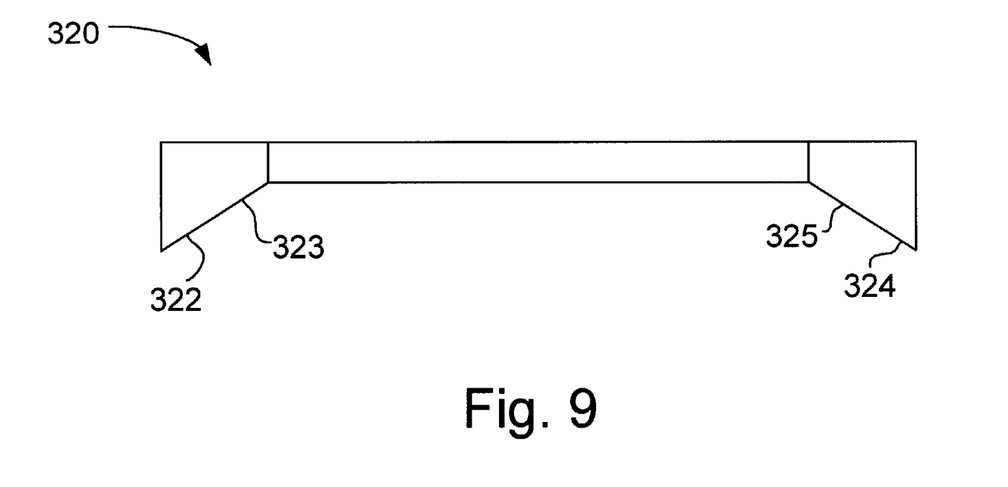
FIGS. 9–10 illustrate top and front views of a visual feedback device in accordance with yet another embodiment of the present invention.
Figure 10:
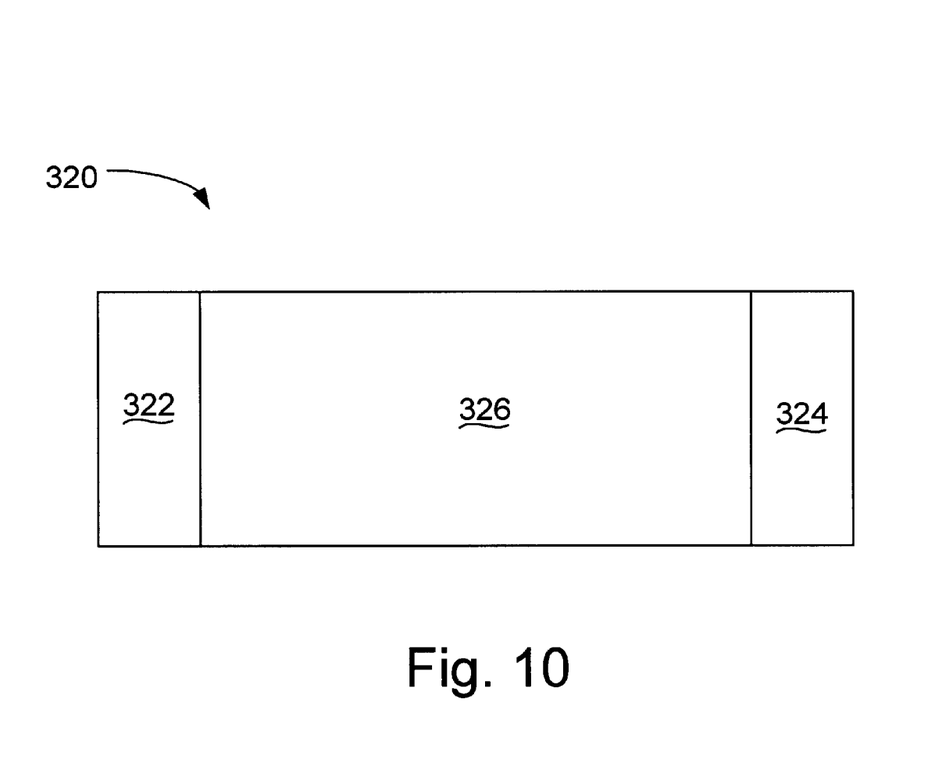

FIGS. 9–10 illustrate another embodiment of a viewer position and orientation feedback device 320 capable of providing feedback similar to that described above with reference to FIGS. 7–8. FIG. 10 provides a front-view of feedback device 320 (i.e., the view apparent to a properly situated viewer), with the active areas 322 and 324 directed towards the viewer. A center portion 326 may display a constant logo, while the active areas 322 and 324 provide the orientation and/or position feedback important to the present invention.

FIG. 9 provides a top-view of feedback device 320. As seen therein, the active areas 322 and 324 are formed having inclined surfaces 323 and 325. By selecting the angle of incline for surfaces 323 and 325 appropriately, a "sweet spot" is formed where the viewer is located in the proper orientation. The available field of view provided by active areas 322 and 324 (and thus the viewer feedback area) will depend upon the construction of and material chosen for making the active areas 322 and 324. Thus, it is preferable that the angle of incline for surfaces 323 and 325 be selected to take advantage of the available field of view. That is, the angle of incline should be selected to provide the viewer feedback in those areas were he or she would most likely be situated. However, it will be appreciated that the field of view provided by active areas 322 and 324 may be such that no incline (i.e., flat surfaces) is even necessary. In any event, those skilled in the art will understand the details necessary for selecting the suitable angle of incline and achieving the desired field of view.

Another particular embodiment that can be described with reference to FIGS. 9 and 10 is implemented such that the center portion 326 is a center active area 326. In one preferred implementation of this embodiment, the viewer feedback is accomplished through a multi-phase (animated, 3D, 4D, etc.) lenticular device. In this embodiment, the lenticular device will display a finite number of images over a suitable viewing range. For example, a total of 28 image phases over a total viewing angle of 58 degrees (i.e., plus and minus 29 degrees from the center viewing axis) would be suitable. When used with a computer monitor, for example, the feedback device 320 should be viewed in the direction of its center active area 326 at a distance of about 22 inches from within a circle having a radius of about 4 inches.

In this embodiment, the center active area 326 is intended to guide the user to maintain his or her eye position near a line orthogonal to the plan of the feedback device 320 and originating at the center of the center active area 326. For example, an optimal eye position may be plus or minus 10.25 degrees from this orthogonal center line. When the user's eyes are within this optimal angle, a positive message such as "GOOD CENTER POSITION" is visible to the user within the center active area 326. As the user's eye position moves to either side of the optimal angle, a meaningful message such as "MOVE RIGHT" would become visible to the user.

The left and right active areas 322 and 324 are intended to work in conjunction with one another to guide the user in maintaining a proper distance from the feedback device 320. Viewing the right-most active area 324 from the optimal distance (e.g., about 22 inches) along the orthogonal center line, the right-most active area 324 displays a positive message such as "GOOD DISTANCE" within a predefined viewing range, e.g., a viewing angle of about 15 degrees plus or minus 10 degrees to the left of a line orthogonal to near center of the right active area 324. Outside of this range, a meaningful message such as "CHECK CENTER POSITION AND MOVE CLOSER" is displayed. The left-most active area 322 would function in an analogous manner.

The embodiments of the present invention described above are "stand alone" feedback devices that work independent of the computer system to provide real-time feedback to a user of the computer system. This feedback enables the user to achieve an ergonomic environment with respect to his or her position and orientation to the computer system. Additional aspects of the present invention further contemplate integrating the position and orientation information into ergonomic software executing upon the computer system. The ergonomic software can utilize the position and orientation information to optimize the computer system setup (e.g., display font size, brightness, etc.), as well as provide additional feedback through the computer system to the user.

Figure 11:
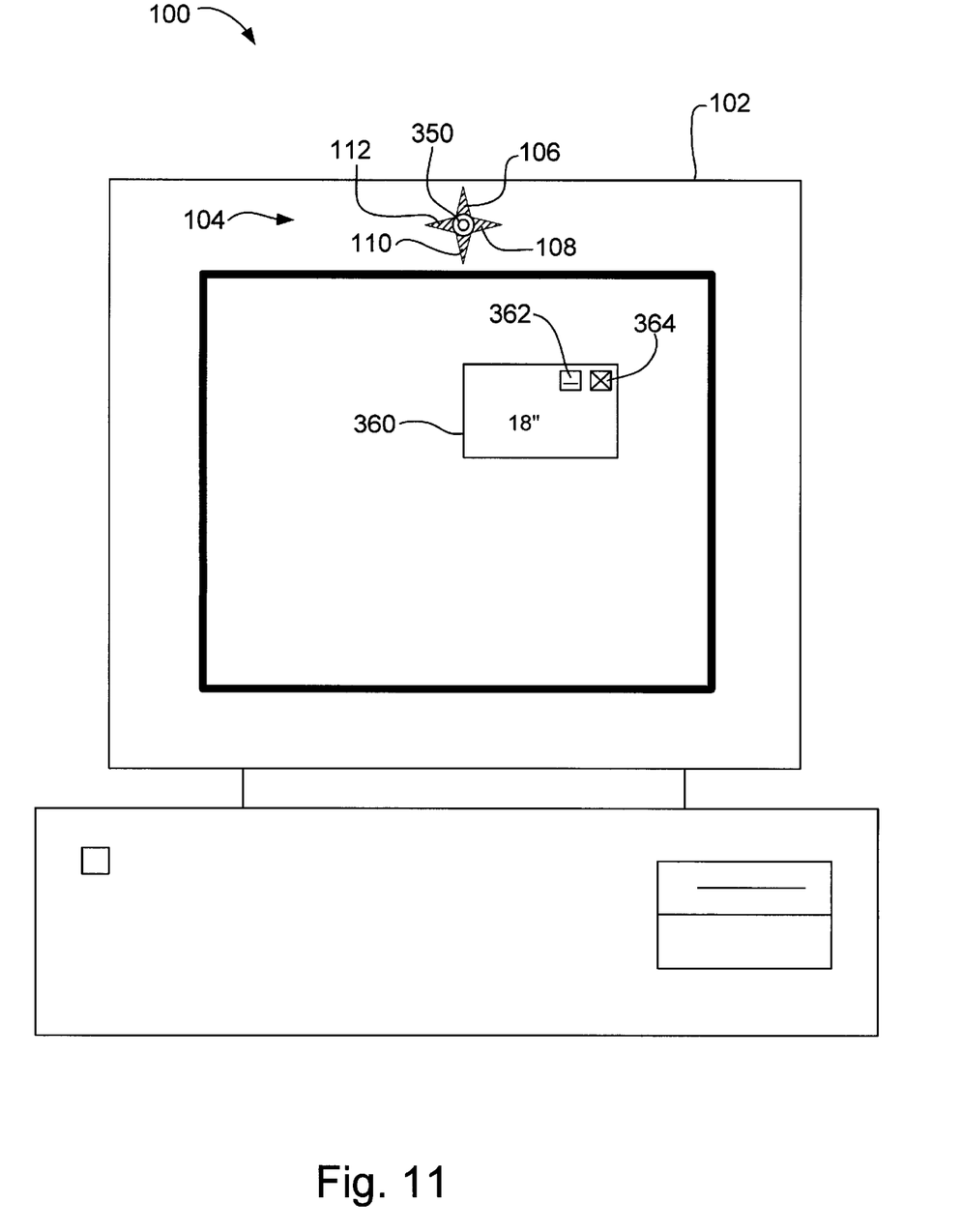
FIG. 11 illustrates a computer system having a distance position sensor in accordance with a separate embodiment of the present invention.
Figure 12:
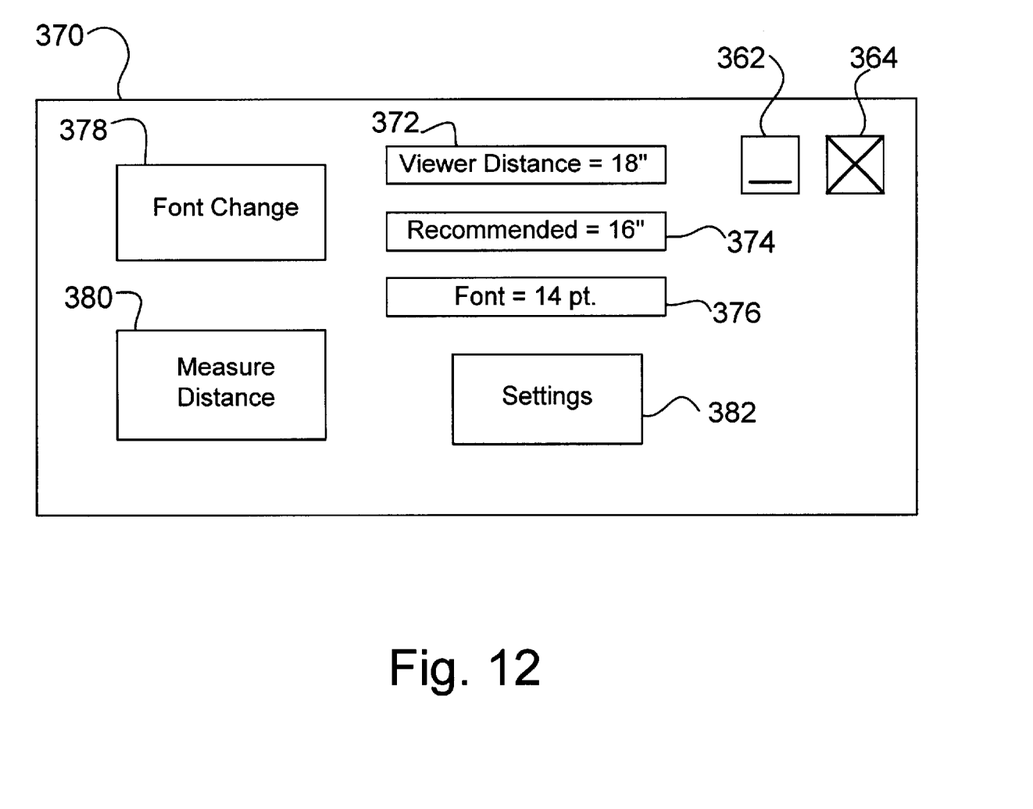
FIG. 12 illustrates an ergonomic software display window generated by the computer system of FIG. 11 when executing the ergonomic software of the present invention.

Turning to FIGS. 11–12, one embodiment of the above-described ergonomic software in accordance with the present invention will now be described. FIG. 11 illustrates a computer system 100 having a display screen 102, a cluster 104 of four light sources 106–112 embedded within the display screen 102, and a viewer position sensor 350 disposed at about the center of the cluster 104. The viewer position sensor 350 is operable to measure the distance of an object properly oriented in front of the position sensor 350. As will be appreciated, a number of such distance measurement devices exist, such as sonic and infrared measurement systems. Shown on the display screen 102 is an ergonomic software icon 360 having a minimize/maximize button 362 and a close button 364, and also a display of the viewer's position from the display screen 102.

Selecting the minimize/maximize button 362 opens up an ergonomic software window such as the window 370 shown in FIG. 12. The ergonomic software window 370 displays a viewer distance 372, a recommended viewer distance 374, a current font setting 376, a font change button 378, a measure distance button 380, and a settings button 382. The viewer distance 372 displays the most recently measured distance of the viewer from the viewer position sensor 350. For example, in certain embodiments the measurement system is continuous and the viewer distance will constantly vary with the viewer position. However, in other embodiments the viewer distance 372 will only update when the measure distance button 380 is selected.

The recommended distance 374 displays a recommended viewer position that is either provided by the ideal visual ergonomic software or can be set by the viewer through the settings button 382. The current font setting 376 preferably displays the font size of text displayed in an active window present on the display 102. Selecting the measure distance button 380 forces the position sensor 350 to measure (if possible) the distance from the viewer to the display screen 102. Once measured, the viewer distance 372 is updated and a suitable font size is selected. Selecting the font change button 378 immediately after selecting the measure distance 380 will change the font size of the corresponding text to a recommended font size based upon the viewer distance and the chosen settings.

Although only a few embodiments of the present invention have been described in detail herein, it should be understood that the present invention may be embodied in many other specific forms without departing from the spirit or scope of the invention. Therefore, the present examples are to be considered as illustrative and not restrictive, and the invention is not to be limited to the details given herein, but may be modified within the scope of the appended claims.

What is claimed is:

1. A visual ergonomic system arranged to assist a viewer in properly positioning themselves with respect to a device the viewer is operating, the visual ergonomic system comprising a visual feedback device capable of providing a plurality of images to a viewer of the display screen, a specific image perceived by the viewer being dependent upon a position of the viewer with respect to the device being operated by the viewer, the specific image perceived by the viewer being indicative of whether the viewer is properly positioned with respect to the device being operated by the viewer.

2. A visual ergonomic system as recited in claim 1 wherein the position of the viewer with respect to the device being operated by the viewer corresponds to a distance separating the viewer from the device being operated by the viewer.

3. A visual ergonomic system as recited in claim 2 wherein the plurality of images includes a first image of five collinear filled circles that is perceived at a first distance separating the viewer from the device being operated by the viewer, a second image of three collinear filled circles that is perceived at a second distance separating the viewer from the device being operated by the viewer, and a third image of a single filled circle that is perceived at a third distance separating the viewer from the device being operated by the viewer.

4. A visual ergonomic system as recited in claim 3 wherein the first distance is greater than the second distance, and the second distance is greater than the third distance.

5. A visual ergonomic system as recited in claim 1 wherein the position of the viewer with respect to the device being operated by the viewer includes an orientation of the viewer in front of the device being operated by the viewer.

6. A visual ergonomic system as recited in claim 5 wherein the visual feedback device includes four light sources arranged such that a) when the viewer is substantially properly oriented with respect to the visual feedback device, the viewer will perceive an image of all four light sources illuminated, b) when the viewer is oriented at a position above the proper vertical orientation, the viewer will perceive that the illumination intensity of an uppermost light source has changed with respect to the image perceived when properly oriented, c) when the viewer is oriented at a position below the proper vertical orientation, the viewer will perceive that the illumination intensity of a lowermost light source has changed with respect to the image perceived when properly oriented, d) when the viewer is oriented at a position substantially to the right of the proper horizontal orientation, the viewer will perceive that the illumination intensity of a rightmost light source has changed with respect to the image perceived when properly oriented, and e) when the viewer is oriented at a position substantially to the left of the proper horizontal orientation, the viewer will perceive that the illumination intensity of a leftmost light source has changed with respect to the image perceived when properly oriented.

7. A visual ergonomic system as recited in claim 6 wherein the intensity of any given light source is substantially inversely related to the corresponding variance of the viewer from the proper orientation.

8. A visual ergonomic system as recited in claim 6 wherein each light source has two levels of intensity such that when the viewer is not properly oriented the corresponding light source appears to not be illuminated.

9. A visual ergonomic system as recited in claim 6 wherein the four light sources are light emitting devices.

10. A visual ergonomic system as recited in claim 9 wherein the four light sources are embedded within opaque material and arranged such that each light source has two levels of intensity so that when the viewer is not properly oriented the corresponding light source appears to not be illuminated.

11. A visual ergonomic system as recited in claim 9 wherein the visual feedback device further includes lenses formed covering the four light sources, the lenses capable of focusing light generated by the four light sources to achieve the desired results.

12. A visual ergonomic system as recited in claim 5 wherein the visual feedback device is a light reflecting device.

13. A visual ergonomic system as recited in claim 12 wherein the specific image perceived by the viewer of the device being operated by the viewer includes text indicating the orientation of the viewer.

14. A visual ergonomic system as recited in claim 12 wherein the specific image perceived by the viewer of the device being operated by the viewer adheres to a color code indicating the orientation of the viewer.

15. A visual ergonomic system as recited in claim 14 wherein the color code includes green, yellow, and red, green indicating proper viewer orientation, yellow indicating questionable viewer orientation, and red indicating improper viewer orientation.

16. A visual ergonomic system as recited in claim 1 wherein the feedback device is formed within a housing of the device being operated by the viewer.

17. A visual ergonomic system as recited in claim 1 wherein the feedback device is formed as a unit separate from but attachable to the device being operated by the viewer.

18. A visual ergonomic system as recited in claim 1 wherein the feedback device is positioned substantially at a top, central point of the device being operated by the viewer.

19. A visual ergonomic system as recited in claim 1 wherein the device being operated by the viewer is a computer having a display screen.

20. A visual ergonomic system as recited in claim 1 wherein the device being operated by the viewer is a television.

21. A computer system comprising:
    a housing;
    a central processing unit (CPU) disposed in said housing;
    a display screen coupled to said CPU and disposed in said housing;
    a measurement device operable to sense a user position with respect to the computer system, the measurement device coupled to the CPU; and
    a computer readable medium coupled to the CPU, the computer readable medium storing computer executable instructions for:
        generating an image suitable for display on the display screen coupled to the CPU, the image being a function of user position information generated by the measurement device operable to sense a user position with respect to the computer system;
        monitoring the user position information generated by the measurement device; and
        updating the image suitable for display on the display screen in response to changes in the user position.

22. A computer system as recited in claim 21 wherein said computer system is a portable computer system.

23. A computer system as recited in claim 22 wherein said housing is suitable for hand-held use.

24. A computer system as recited in claim 23 wherein said computer system is a personal digital assistant (PDA).

25. A computer system as recited in claim 21 wherein said measurement device is disposed within said housing.

26. A computer system as recited in claim 21 wherein said measurement device is disposed remotely from said housing.

27. A computer system as recited in claim 21 wherein a first portion of said measurement device is disposed within said housing and a second portion of said measurement device is disposed remotely from said housing.

28. A method for ergonomically enhancing an environment for a viewer of a device being operated by the viewer, the method comprising the step of:
    rendering a first image that can be perceived by the viewer of the device being operated by the viewer when the viewer is situated in an ergonomically correct orientation with respect to the device being operated by the viewer.

29. A method as recited in claim 28, the method further comprising the step of:
    rendering a second image that can be perceived by the viewer of the device being operated by the viewer when the viewer is situated in an ergonomically improper orientation with respect to the device being operated by the viewer,
    whereby the viewer is continuously provided visual feedback regarding an ergonomic status of the viewer's orientation with respect to the device being operated by the viewer.

30. A method as recited in claim 28, the method further comprising the steps of:
    rendering a second image that can be perceived by the viewer of the device when the viewer is located above a vertically correct ergonomic orientation with respect to the device;
    rendering a third image that can be perceived by the viewer of the device when the viewer is located below a vertically correct ergonomic orientation with respect to the device;
    rendering a fourth image that can be perceived by the viewer of the device when the viewer is located to the left of the horizontally correct ergonomic orientation with respect to the device; and
    rendering a fifth image that can be perceived by the viewer of the device when the viewer is located to the left of the horizontally correct ergonomic orientation with respect to the device.

* * * * *